(12) United States Patent
Suzuki et al.

(10) Patent No.: US 6,890,327 B2
(45) Date of Patent: May 10, 2005

(54) DISPOSABLE DIAPER

(75) Inventors: Seiji Suzuki, Kagawa-ken (JP); Hiroyuki Soga, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 22 days.

(21) Appl. No.: 09/183,087

(22) Filed: Oct. 30, 1998

(65) Prior Publication Data

US 2001/0018580 A1 Aug. 30, 2001

(30) Foreign Application Priority Data

Oct. 31, 1997 (JP) ............................................. 9-300856

(51) Int. Cl.[7] .......................... A61F 13/15; A61F 13/20
(52) U.S. Cl. .............................. 604/385.28; 604/385.29
(58) Field of Search ...................... 604/385.2, 397–398, 604/385.1, 393–396, 385.23–385.3

(56) References Cited

U.S. PATENT DOCUMENTS

| | | | | |
|---|---|---|---|---|
| 4,695,278 A | * | 9/1987 | Lawson | |
| 4,753,646 A | | 6/1988 | Enloe | |
| 5,026,364 A | * | 6/1991 | Robertson | |
| 5,575,785 A | * | 11/1996 | Gryskiewicz et al. | .... 604/385.2 |
| 5,593,401 A | | 1/1997 | Sosalla et al. | |
| 5,672,166 A | | 9/1997 | Vandermoortele | |

FOREIGN PATENT DOCUMENTS

| | | | |
|---|---|---|---|
| GB | 2251172 | * | 7/1992 |
| JP | 2-174845 | * | 7/1990 |
| JP | 3-136653 | | 6/1991 |

OTHER PUBLICATIONS

Copy of European Search Report dated Aug. 1, 2000.

* cited by examiner

Primary Examiner—Karin Reichle
(74) Attorney, Agent, or Firm—Butzel Long

(57) ABSTRACT

A disposable diaper including a topsheet, a backsheet and a core disposed therebetween. A pair of outer side barrier cuffs and a pair of inner side barrier cuffs lying more inwardly of the outer side barrier cuffs are formed adjacent transversely opposite side edges and extend longitudinally thereof. Each of the outer side barrier cuffs has its longitudinally opposite ends covered with a pair of end barrier flaps that are positioned adjacent longitudinally opposite ends of the diaper so as to form front and rear pockets, respectively. The inner side barrier cuffs are shorter than the outer side barrier cuffs.

7 Claims, 3 Drawing Sheets

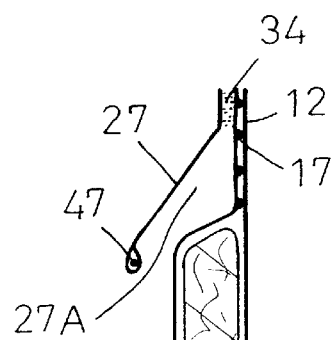
FIG.3
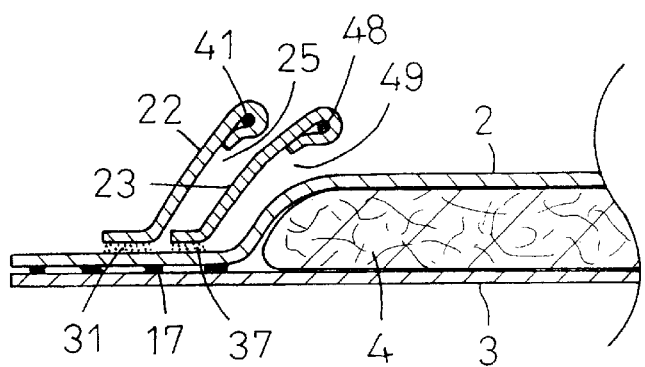
FIG.2
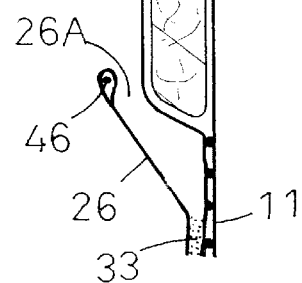

DISPOSABLE DIAPER

BACKGROUND OF THE INVENTION

This invention relates to disposable diapers for absorbing and containing excretion.

Japanese Patent Application Disclosure Gazette (Kokai) No. Hei3-136653 discloses an integral or unitary disposable diaper having a topsheet with a pair of side barrier cuffs formed thereon and extending along transversely opposite side edges of the topsheet and a pair of end barrier flaps extending along longitudinally opposite ends thereof. Both the barrier cuffs and the barrier flaps are adapted to be collapsible inwardly of the diaper. The side barrier cuffs extend between the longitudinally opposite ends of the diaper while the end barrier flaps extend between the transversely opposite sides of the diaper and cover longitudinally opposite ends of the side barrier cuffs.

The side barrier cuffs are longitudinally elastic so that the side barrier cuffs are normally biased under the effect of their longitudinal elasticity to rise up on the topsheet-and thereby to form pockets opening inwardly of the diaper between the side barrier cuffs and the topsheet when the diaper is put on a wearer's body. However, side barrier cuffs alone are not effective to prevent excretion from leaking from the sides of the diaper, even if side flaps extending outwardly of the side barrier cuffs are provided with elastic members so as to contact the side flaps against a wearer's skin.

SUMMARY OF THE INVENTION

In view of the above problem, it is an object of the invention to prevent excretion from leaking sideways in diapers.

According to the invention, there is provided a diaper comprising a laminate of a liquid-permeable topsheet, a liquid-impermeable backsheet and a liquid-absorbent core disposed therebetween. The laminate has an external shape defined by longitudinally opposite ends and transversely opposite side edges extending between the longitudinally opposite ends. The laminate includes a pair of first side barrier cuffs formed on an inner surface adjacent the opposite side edges and extending longitudinally of the laminate so as to be collapsible inwardly of the laminate, and a pair of end barrier flaps placed in the proximity of the longitudinally opposite ends of the laminate so as to extend between the transversely opposite side edges of the laminate and to cover the longitudinally opposite ends of the pair of first side barrier cuffs, respectively, the end barrier flaps being partially bonded to the inner surface of the laminate and thereby forming a pair of pockets adapted to open inwardly of the laminate. A pair of second side barrier cuffs are formed inwardly of the first side barrier cuffs on the inner surface of the laminate. Each of the second side barrier cuffs extends from a longitudinally middle zone of the laminate in opposite directions longitudinally of the laminate. An outer edge of each second side barrier cuff is bonded to the inner surface of the laminate while an inner edge of each second barrier cuff extends in parallel to the outer edge and is longitudinally elastic so as to be collapsible inwardly of the laminate. Each of the second side barrier cuffs has a dimension between longitudinally opposite ends thereof which is shorter than that of the first side barrier cuffs and is bonded to the inner surface of the laminate so that the longitudinally opposite ends of the second side barrier cuffs lie more inwardly of the laminate than the longitudinally opposite ends of the first side barrier cuffs.

According to a preferred embodiment of the invention, the longitudinally opposite ends of the second side barrier cuffs lie more inwardly of the laminate than the longitudinally opposite ends of the first side barrier cuffs, respectively, by 20 mm or more.

According to another preferred embodiment of the invention, the first side barrier cuffs, the second side barrier cuffs and the end barrier flaps form pockets that are made of liquid-resistant materials.

BRIEF DESCRIPTION OF THE DRAWINGS

Details of a disposable diaper according to the invention will be more fully understood from the description given hereunder with reference to the accompanying drawings, in which:

FIG. 2 is a sectional view taken along a line II—II in FIG. 1;

FIG. 3 is a sectional view taken along a line III—III in FIG. 1; and

DESCRIPTION OF THE PREFERRED EMBODIMENTS

Figure 1:
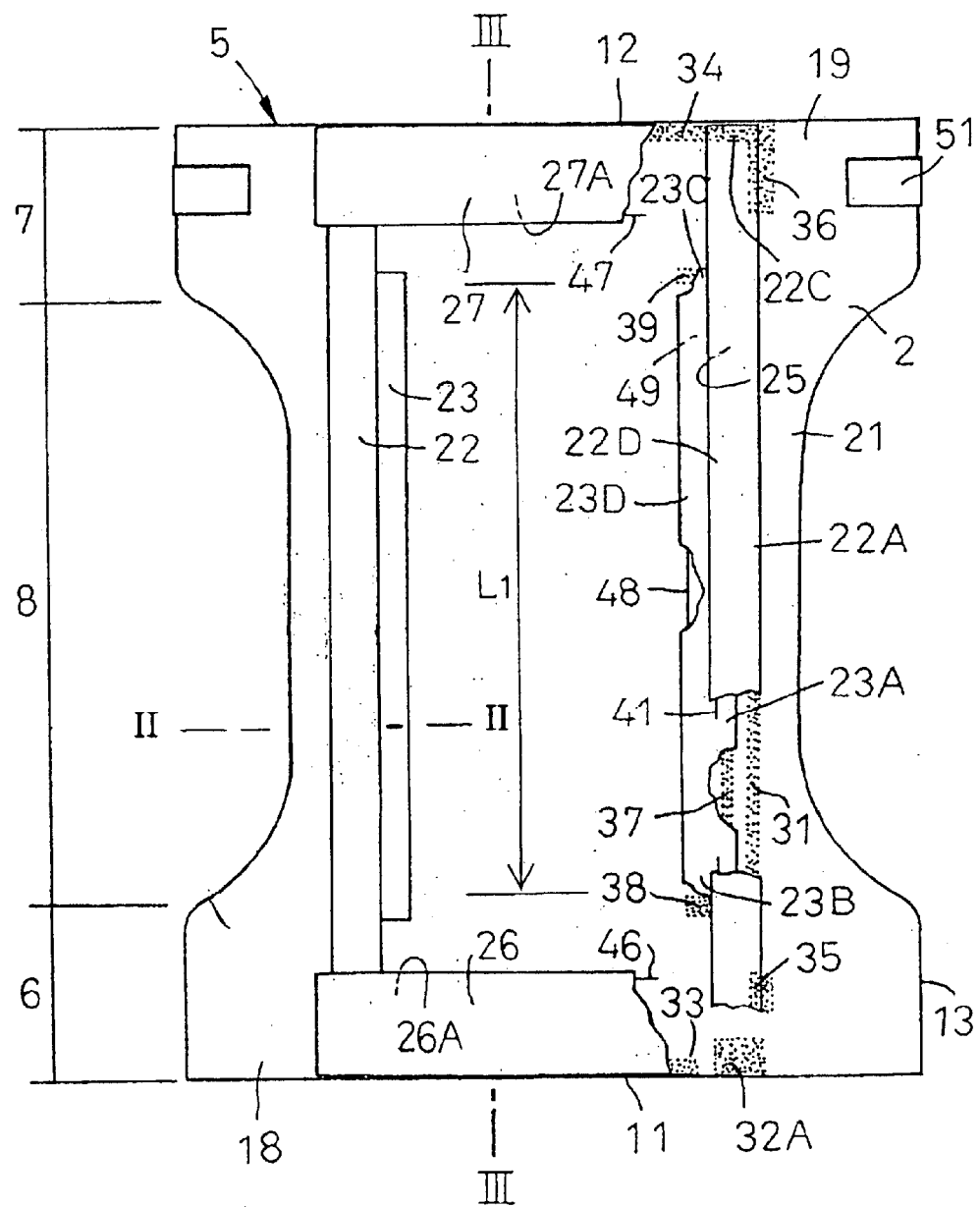
FIG. 1 is a partly cutaway plan view depicting a diaper according to the invention.

FIGS. 1, 2 and 3 are respectively a partly cutaway plan view depicting an embodiment of a disposable diaper according to the invention, a sectional view taken along a line II—II in FIG. 1 and a sectional view taken along a line III—III in FIG. 1. The disposable diaper shown in these figures includes a main body 5 in the form of a laminate comprising a liquid-permeable topsheet 2, a liquid-impermeable backsheet 3 and a liquid-absorbent core 4 disposed between these two sheets 2, 3. The main body 5 has a front waist region 6, a rear waist region 7 and a crotch region 8 extending between these two waist regions 6, 7. The main body 5 is defined by longitudinally opposite ends 11, 12 extending in the transverse direction of the front and rear waist regions 6, 7, respectively, and transversely opposite side edges 13, 13 extending between these longitudinally opposite ends 11, 12. The respective side edges 13, 13 are inwardly curved in the crotch region 8. The topsheet 2 and the backsheet 3 are placed one upon another and intermittently bonded together by adhesive 17 means such as a hot melt adhesive agent along their portions extending laterally beyond transversely opposite edge of the core 4 so as to forth longitudinally opposite end flaps 18, 19 and transversely opposite side flaps 21, 21.

The main body 5 includes on its inner surface outer and inner side barrier cuffs 22, 22; 23, 23 extending in parallel to the side edges 13, 13, respectively. On the inner surface, the main body 5 further includes front and rear pockets 26A, 27A both opening inwardly of the diaper. The pockets 26A, 27A comprise a pair of end barrier flaps 26, 27 extending on the inner surface in the transverse direction of the front and rear waist regions 6, 7, respectively, so that the pockets 26A, 27A may be defined between the respective end barrier flaps 26, 27 and the topsheet 2. Zones represented by many dots are hot melt adhesive applied zones along which the end barrier flaps 26, 27 and the side barrier 22, 22; 23, 23 are bonded to the underlying component of the diaper.

Each of the outer end barrier flaps 22, 22 is formed from a strip of liquid-resistant sheet extending to the vicinity of the longitudinally opposite ends 11, 12 of the main body 5.

Figure 4:
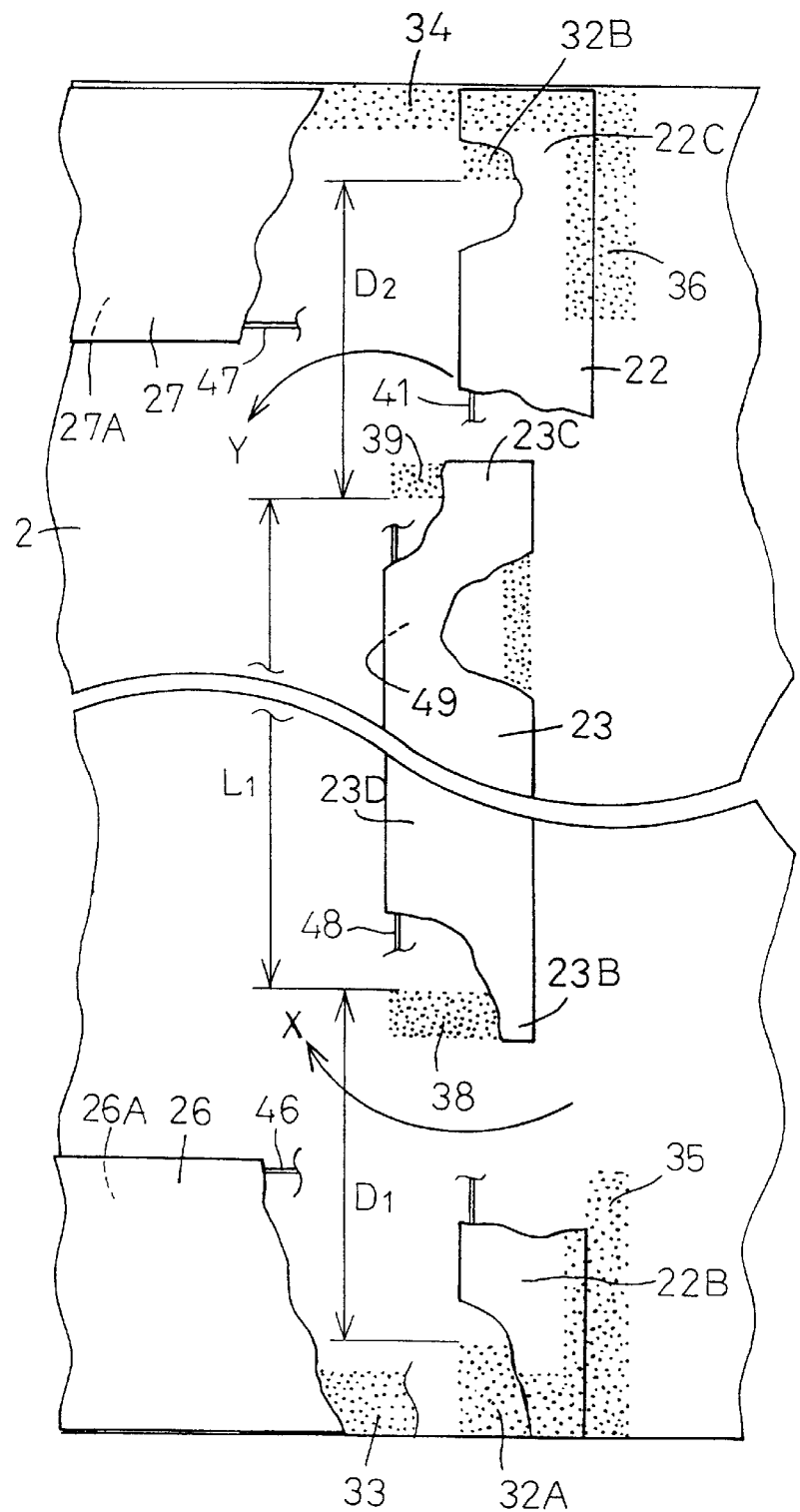
FIG. 4 is a partly cutaway enlarged plan view depicting the diaper.

Outer side edge 22A and longitudinally opposite ends 22B, 22C (22B is shown in FIG. 4) of the side barrier cuffs 22 are bonded to the topsheet 2 along first adhesive applied zone 31 and second adhesive applied zones 32A, 32B (32B is shown in FIG. 4) lying in the proximity of the longitudinally opposite ends 11, 12, respectively. Inner side edge 22D of the side barrier cuff 22 lies more inwardly of the main body 5 than the outer side edge 22A and a longitudinally extending first elastic member 41 is secured under appropriate tension to an inner surface of the inner side edge 22D. With the outer side barrier cuff 22 in the arrangement as described above, the inner side edge 22D is spaced upward from the topsheet under the effect of the elastic member 41 between the longitudinally opposite ends 22B, 22C so as to form a first pocket 25 opening inwardly of the main body 5 when the diaper is put on a wearer's body.

The end barrier flaps 26, 27 respectively that form the front and rear pockets 26A, 27A are substantially rectangular liquid-resistant sheets. Longitudinally opposite ends of the respective end barrier flaps 26, 27 cover the longitudinally opposite ends 22B, 22C of the respective outer side barrier flaps 22. The end barrier flaps 26, 27 are bonded to the inner surface of the main body 5 along third and fourth adhesive applied zones 33, 34 that extend along the longitudinally opposite ends 11, 12 of the main body 5, on one hand, and along fifth and sixth adhesive applied zones 35, 36 respectively extending from the longitudinally opposite ends 11, 12 inwardly of the main body 5. The fifth and sixth adhesive applied zones 35, 36 are formed on upper surfaces of the respective collapsed outer side barrier cuff 22 and/or the upper surface of the topsheet 2 extending outward beyond the outer side edges of the side barrier cuffs 22. Third and fourth elastic members 46, 47 are secured under appropriate tension to inner surfaces of the respective end barrier flaps 26, 27 along their inner edges that extend along a wearer's waist line.

Each of the inner side barrier cuffs 23 is formed from a strip of liquid-resistant sheet having its outer side edge 23A as well as its longitudinally opposite ends 23B, 23C bonded to the inner surface of the main body 5 along longitudinally extending seventh adhesive applied zone 37 and along eighth and ninth adhesive applied zones 38, 39 formed adjacent longitudinally opposite ends of the adhesive applied zone 37. An inner side edge 23D lies more inwardly of the main body 5 than the outer side edge 23A. A longitudinally extending second elastic member 48 is secured under appropriate tension to the inner surface of the side barrier cuff 23 along the inner side edge 23D. The inner side barrier flap 23 forms a second pocket 49 that is adapted to open inwardly of the diaper when the diaper is put on a wearer's body.

FIG. 4 is a partly cutaway enlarged plan view depicting the diaper of FIG. 2. Each of the inner side barrier cuffs 23 has a region extending between its longitudinally opposite ends 23B, 23C, that are both bonded to the topsheet 2, which is spaced from the upper surface of the topsheet 2 and thereby defines a second pocket 49 that opens inwardly. The longitudinally opposite ends 23B, 23C are respectively spaced from portions of the longitudinally opposite ends 22B, 22C at which the outer side barrier cuff 22 is bonded to the topsheet 2 by distances $D_1$, $D_2$. These distances $D_1$, $D_2$ respectively correspond to the distances from longitudinal inner edges of the second adhesive applied zones 32A, 32B to longitudinal inner edges of the eighth and ninth adhesive applied zones 38, 39, i.e., to the region L1 of the inner side barrier cuff 23. For the inner side barrier cuff 23, $D_1$, $D_2$ are preferably 20 mm or longer and not entirely covered with the strips of sheet 26, 27, respectively, as in the embodiment shown by FIG. 4. Compared to the length $L_1$ over which the inner side barrier cuff 23 can open, a length over which the outer side barrier cuff 22 can open is relatively long since this distance corresponds to a sum of $L_1$, $D_1$ and $D_2$.

With the diaper constructed as described above, the inner and outer side barrier cuffs 22, 23 are biased by contraction of the first and second elastic members. 41, 48 so as to rise up on the upper surface of the topsheet 2 when the diaper is longitudinally curved on a wearer's body with the topsheet 2 lying inside. The outer side barrier cuff 22, the front pocket 26 and rear pocket 27 serve to prevent excretion from leaking beyond a periphery of the diaper. The inner side barrier cuffs 23 serve to prevent, particularly in the crotch region 8, excretion from flowing sideways and thereby to reduce the amount of excretion which would otherwise stay in the proximity of the outer side barrier cuff 22. Each of the inner side barrier cuffs 23 has an open longitudinal dimension substantially equal to the previously mentioned length L1 and is shorter than a substantial dimension of the outer side barrier cuff 22 as measured in parallel to the $L_1$. Transversely of the diaper, an amount of excretion which has overflown the inner side barrier cuffs 23 to the outer side barrier cuff 22 may continue to flow along these outer side barrier cuffs 22 toward one of the longitudinally opposite ends 11, 12 of the main body 5. Excretion may then flow inwardly of the diaper as indicated by arrows X, Y (See FIG. 4) since the inner side barrier cuffs 22 are not present in the proximity of the ends 11, 12. In this way, the amount of excretion at the outer side barrier cuffs 22 can be reduced end thereby an amount of excretion which would otherwise leak beyond the side barrier cuffs 22 can be reduced.

In the diaper according to the invention, the liquid-resistant sheets employed as the material for the inner and outer side barrier cuffs 22, 23 as well as the end barrier flaps 26, 27 can include various sheets which function as substantially liquid-impermeable or liquid-permeation-retardant sheets during practical use of the diaper. The outer side barrier cuffs 22 and the longitudinally opposite end barrier flaps 26, 27 may be bonded together over portions of their overlapping zones or substantially over these entire zones. An alternative embodiment of the invention is also conceivable in which the front and rear end barrier flaps 26, 27 are not provided with the third and fourth elastic members 46,47, respectively. At least one of the front and rear waist regions 6,7, may have elastic members extending along a wearer's waist line that are secured under appropriate tension to the longitudinally opposite end flaps 18, 19. FIG. 1 depicts the diaper of so-called "open type" in which the rear waist region 7 is provided on its transversely opposite side edges with tape fasteners 51, that are adapted to be releasably fastened to an outer surface of the front waist region 6. It should be understood that the invention is not limited to the illustrated embodiment but is also applicable to the diaper of pull-on or shorts type.

In the disposable diaper according to the invention, each of the side barrier cuffs which function to prevent excretion from leaking sideways is provided in the form of a combination of the inner and outer side barrier cuffs of which the longitudinal dimensions are different from each other. Therefore, leakage of excretion can be effectively prevented. An amount of excretion having overflown the inner side barrier cuffs to the associated outer side barrier cuffs may continue to flow along outer side barrier cuffs toward one of the longitudinally opposite ends of the diaper. In the proximity of these ends, the inner side barrier cuffs are not present and therefore the amount of excretion can flow inwardly of the diaper without being restricted by the inner side barrier cuffs. By guiding the flow of excretion inwardly of the diaper, the amount of excretion which would otherwise stay in the proximity of the outer side barrier cuffs can be reduced and thereby sideways leaking of excretion can be further effectively prevented.

What is claimed is:

1. A disposable diaper comprising:

a liquid-permeable topsheet, a liquid-impermeable backsheet and a liquid-absorbent core disposed therebetween, said diaper having a peripheral shape defined by longitudinally opposite ends and transversely opposite side edges extending between said longitudinally opposite ends, said diaper including a pair of elasticized first side barrier cuffs formed on an inner surface thereof which first side barrier cuffs are adjacent said respective side edges and extend longitudinally so as to be collapsible inwardly to define a pair of first side pockets adapted to open inwardly, a pair of elasticized second side barrier cuffs formed on the inner surface thereof, which second side barrier cuffs are located inwardly of said first side barrier cuffs, respectively, and extend parallel to said first side barrier cuffs so as to be collapsible inwardly to define a pair of second side pockets adapted to open inwardly, and a pair of end barrier flaps provided in proximity to said respective longitudinally opposite ends so as to extend between said transversely opposite side edges, said end barrier flaps being partially bonded to said inner surface and thereby forming a pair of third end pockets adapted to open inwardly, each of said first side barrier cuffs extending to said longitudinally opposite ends of said diaper and each of said second side barrier cuffs extending to locations spaced apart inwardly of said longitudinally opposite ends of said diaper, longitudinally opposite ends of each of said second side barrier cuffs defining longitudinally opposite ends of said second side pockets and longitudinally opposite ends of said respective first side barrier cuffs defining longitudinally opposite ends of said first side pockets, and said end barrier flaps cover the longitudinally opposite ends of said first side barrier cuffs, respectively.

2. The diaper according to claim 1, wherein said longitudinally opposite ends of said second barrier cuffs lie more inwardly on said diaper than said longitudinally opposite ends of said first side barrier cuffs respectively, by at least 20 mm.

3. The diaper according to claim 1, wherein said first side barrier cuffs, said second side barrier cuffs and said end barrier flaps forming said pockets are made of liquid-resistant materials.

4. The diaper according to claim 2, wherein said first side barrier cuffs, said second side barrier cuffs and said end barrier flaps forming said pockets are made of liquid-resistant materials.

5. The diaper according to claim 1, wherein said first and second side barrier cuffs are provided along edges thereof with elastic members.

6. The diaper according to claim 1, wherein said end barrier flaps are elasticized.

7. The diaper according to claim 6, wherein said end barrier flaps are provided along inner edges thereof with elastic members.

* * * * *